United States Patent [19]

MacKay et al.

[11] Patent Number: 5,648,219

[45] Date of Patent: Jul. 15, 1997

[54] IMMORTALIZED DENDRITIC CELLS

[75] Inventors: Vivian L. MacKay; Emma E. Moore, both of Seattle, Wash.

[73] Assignee: ZymoGenetics, Inc., Seattle, Wash.

[21] Appl. No.: 479,882

[22] Filed: Jun. 7, 1995

[51] Int. Cl.$^6$ .............. C12Q 1/68; C12Q 1/02; C12N 5/02; C12N 15/12

[52] U.S. Cl. .............. 435/6; 435/29; 435/172.1; 435/172.3; 435/325; 435/355

[58] Field of Search .............. 435/6, 240.2, 240.23, 435/29, 172.3, 172.1

[56] References Cited

FOREIGN PATENT DOCUMENTS

| 92/11874 | 7/1992 | WIPO. |
| 93/20185 | 10/1993 | WIPO. |
| 94/28113 | 12/1994 | WIPO. |

OTHER PUBLICATIONS

Inaba et al., *Proc. Natl. Acad. Sci. USA* 90: 3038–3042, 1993.

Lutz et al., *J. Immunol. Methods* 174: 269–279, 1994.

Girolomoni et al., *Eur. J. Dermatol.* 5: 12–15, 1995.

Inaba et al., *J. Exp. Med.* 176: 1693–1702, 1992.

Paglia et al., *J. Exp. Med.* 178: 1893–1901, 1993.

O'Doherty et al., *J. Exp. Med.* 178: 1067–1078, 1993.

Harvey et al., *Oncogene* 8: 2457–2467, 1993.

Tsukada et al., *Oncogene* 8: 3313–3322, 1993.

Karlhofer et al., *J. Exp. Med.* 181: 1785–1795, 1995.

*Primary Examiner*—Christina Y. Chan
*Assistant Examiner*—F. Pierre VanderVegt
*Attorney, Agent, or Firm*—Deborah A. Sawislak; Gary E. Parker; Debra K. Leith

[57] ABSTRACT

The present invention provides an immature dendritic cell line derived from p53 growth suppressor gene deficient animals. The immature dendritic cell line may be induced to become an activated dendritic cell line that will stimulate T-cells to proliferate. The cell line is useful for presentation of antigens involved in autoimmune disease and analysis of peptides that produce a T-cell response.

15 Claims, 1 Drawing Sheet

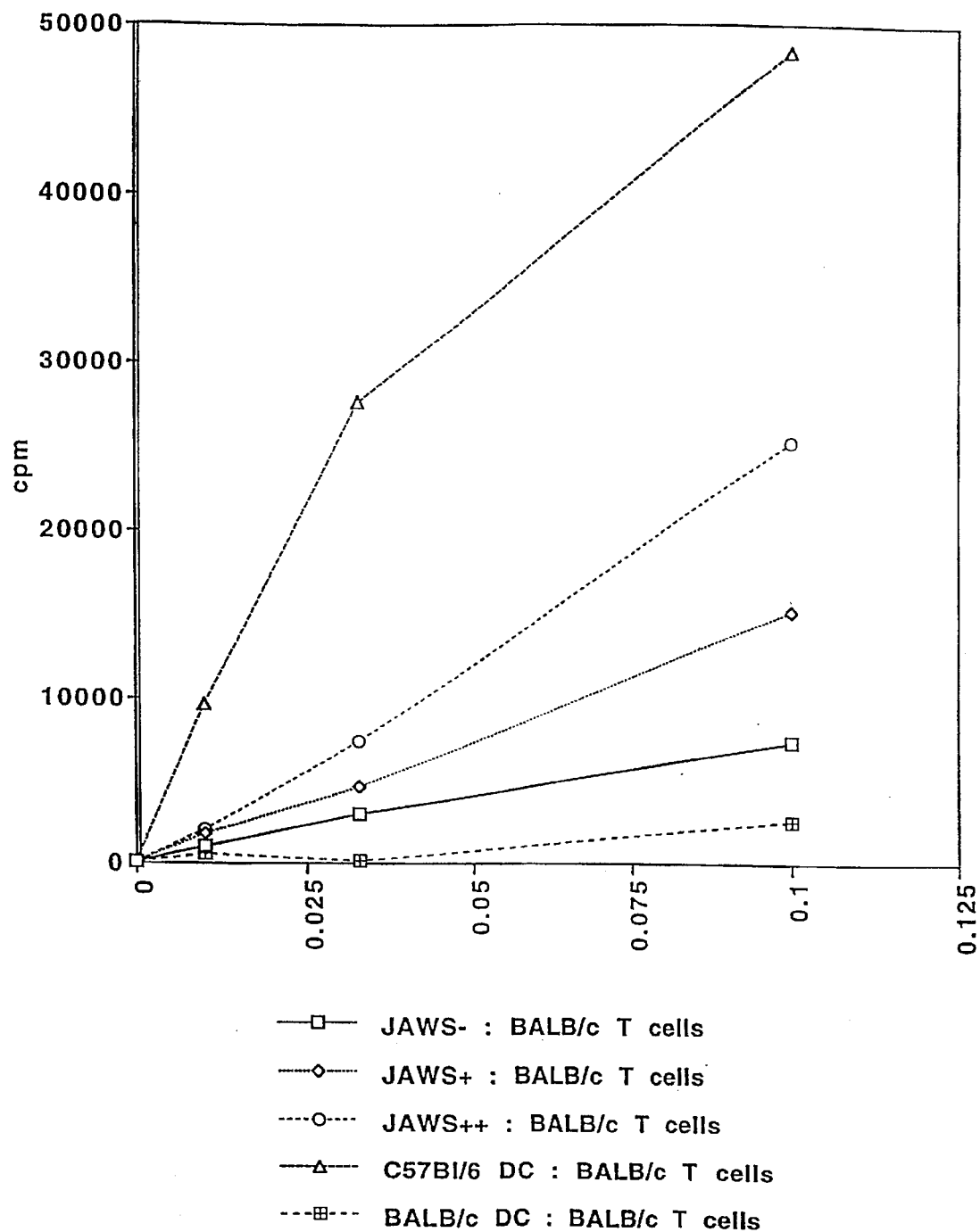

IMMORTALIZED DENDRITIC CELLS

BACKGROUND OF THE INVENTION

Cell lines have played an important role in the development of molecular and cellular biology, particularly in the elucidation of intracellular activities, the effects of extracellular molecules and cell-cell interactions. Cell lines are established stepwise by: explantation of tissue containing a heterogeneous cell population; separation of the cells; isolation of a cell clone; and culturing the cell clone so that the total cell number increases over several generations and the population is uniform in its lineage. For instance, cell cultures may be started from primary tissue culture explants, where heterogeneous cell types separate or migrate from the tissue in liquid medium; or by enzyme digestion of a tissue, resulting in dispersed cell suspensions.

Differentiation is the process of maturation of cells. It is a progressive and dynamic process, beginning with pluripotent stem cells and ending with terminally differentiated cells that progress no further down the cell lineage pathway. A cell's function, phenotype and growth characteristics are affected by the cell's degree of differentiation.

Cells that can be continuously cultured are known as immortalized cells. Immortalized cells have advantages over non-immortalized cells because they can be cultured to provide large numbers of uniform cell populations. Immortalized cells are routinely used for understanding intracellular activities, such as the replication and transcription of DNA, metabolic processes and drug metabolism. Investigation of cellular transmembrane activities, such as, ligand-receptor interactions and signal transduction, is facilitated by access to specific cell types. Immortalized cells are also useful in examining specific cell-cell interactions, such as adhesion, invasion and contact inhibition. However, many cell types have remained recalcitrant to isolation and continuous culture. In addition, many differentiated cells lose some of their differentiated properties (dedifferentiate) in order to regain or retain the ability to proliferate. Thus, if an immortalized cell line were available that could be continuously cultured it would not necessarily express the differentiation functions that make it a valuable tool.

One such cell type that has been difficult to immortalize is the dendritic cell, an antigen presenting cell, and its precursors that are at early stages of differentiation. Steinman et al., WO 93/20185, have disclosed methods for isolating primary dendritic cells and their precursors from tissue. Granucci et al., WO 94/28113, and Paglia et al., *J. Exp. Med.* 178:1893–1901, 1993, have disclosed cell lines isolated from primary cultures and infected with retroviral vectors to immortalize the cells.

Dendritic cells are the most potent antigen presenting cells (APCs) in the immune system. Dendritic cells are the only cells that present antigen to, and activate, naive CD4+ T cells in vivo (Levin et al., *J. Immunol.* 151:6742–6750, 1993). Dendritic cells are found in primary and secondary lymphoid organs (e.g., thymus, lymph nodes, tonsils, Peyer's patches, and spleen), as well as in non-lymphoid organs and tissues (e.g., heart, liver, lung, gut, and in the skin as epidermal Langerhans cells). Dendritic cells are also prevalent in afferent lymph, but are rare in blood. For reviews, see Steinman, *Ann. Rev. Immunol.* 9:271–296, 1991 and Knight et al., *J. Invest. Dermatol.* 99:33S–38S, 1992.

Dendritic cells are thought to originate from a single hematopoietic progenitor cell. As progenitor cells begin the process of differentiation they migrate to selected tissue and/or organs, where they appear to undergo additional differentiation. If isolated from tissue, dendritic cells are immature; that is, the cells are not fully differentiated, are inefficient at antigen presentation, express low levels of MHC Class II molecules and do not stimulate proliferation of T-cells in an allogenic mixed leukocyte reaction (MLR). However, when immature dendritic cells are exposed to foreign proteins, they become capable of taking up and presenting soluble antigen via newly synthesized MHC Class II molecules, and stimulataneously leave their tissue residence and migrate to lymph nodes and spleen. After migrating from the origin tissue, the dendritic cells are mature; that is, they exhibit high levels of MHC Class II, accessory and co-stimulatory molecules, as well as full APC function (Steinman, ibid., 1990 and Ibrahim et al., *Immunol. Today* 16:181–186, 1995). Antigen uptake and processing by dendritic cells are not well understood, however, because of the inability to isolate and culture sufficient numbers of homogeneous dendritic cells or dendritic precursor cells.

Dendritic cells have been implicated as the primary causative cells in a number of different diseases that involve immune responses, including contact sensitivity, tumor immunity, HIV-1 infection and autoimmunity (e.g., Type I diabetes, multiple sclerosis and rheumatoid arthritis). These cells are believed to play a role in graft rejection, where cells from the allograft migrate into the lymphoid organs of the recipient and initiate a deleterious immune response.

Therefore, a need remains in the art for immortalized dendritic cells that can be directly isolated from a tissue source and cultured continuously. There also remains a need for immortalized dendritic precursor cells that can be activated into antigen presenting cells that retain their differentiated properties while continuously being cultured.

SUMMARY OF THE INVENTION

It is an object of the present invention to provide an dendritic cell. The dendritic cells has been deposited at the American Type Culture Collection as JAWS II.

It is a further object of the present invention to provide a dendritic cell that is induced to become an activated dendritic cell. In one embodiment, the dendritic cell is activated using a factor selected from the group consisting of a) tumor necrosis factor-α (TNF-α); (b) interferon-γ (IFN-γ); (c) granulocyte macrophage colony-stimulating factor (GM-CSF); (d) interleukin-4 (IL-4); and (e) a combination of (a), (b), (c) or (d).

Another object of the present invention provides for methods for assaying antigen-specific responder cell stimulation comprising activating the dendritic cells, exposing the activated cells to an exogenous antigen, thereby producing antigen-presenting stimulator cells and measuring activation of the responder cells. In one embodiment, the responder cells are naive or primed T cells. In another embodiment, the activation of the responder cells is determined by measuring responder cell proliferation. In another embodiment, the proliferation of the antigen-presenting stimulator cells is inhibited prior to the step of combining with the responder cells. In another embodiment, the proliferation of the antigen-presenting stimulator cells is inhibited by exposure to γ irradiation or mitomycin C.

In another aspect, the present invention provides for methods for obtaining a dendritic cells that expresses a heterologous MHC class II protein at the cell surface comprising transfecting the dendritic cells with a polynucleotide encoding a heterologous MHC class II protein and selecting a subset of the dendritic cells that expresses the heterologous MHC class II protein at the cell surface, thereby forming selected MHC class II-specific dendritic cells. In another embodiment, the methods comprise the step of eliminating from the dendritic cell genome any region the encodes endogenous MHC class II molecules. In another embodiment, the methods provide activated the selected MHC class II-specific dendritic cells. In another embodiment, the methods comprise before, during or after the step of activating, blocking endogenous MHC class II protein expressed by the selected MHC class II-specific dendritic cells. In another embodiment, after activation, the methods comprise exposing the selected MHC class II-specific dendritic cells to an exogenous antigen, thereby producing selected MHC class II-specific antigen-presenting stimulator cells with responder cells and measuring the stimulation of the responder cells. In another embodiment, the responder cells are T lymphocytes. In another embodiment, the exogenous antigen is a self or non-self antigen that is involved in a T lymphocyte-mediated response. In another embodiment, the exogenous antigen is an autoantigen. In another embodiment, the exogenous antigen is GAD and the heterologous MHC class II protein is an MHC molecule associated with diabetes.

BRIEF DESCRIPTION OF THE DRAWINGS

The Figure illustrates that allogeneic T cells are stimulated to proliferate when exposed to activated JAWS II cells. The stimulation of the allogeneic T cells is highest when JAWS II is induced with TNF-α, IFN-γ, and IL-4 (JAWS++), but still was present in JAWS II cells induced with TNF-α and IFN-γ (JAWS+) and JAWS II induced with TNF-α alone (JAWS-). Syngeneic BALB/c dendritic cells, used as a negative control, did not stimulate proliferation of the BALB/c T cells.

DETAILED DESCRIPTION OF THE INVENTION

Prior to describing the present invention in detail, it may be helpful to define certain terms used herein:

Immature dendritic cell: A dendritic cell that expresses low levels of MHC class II, but is capable of endocytosing antigenic proteins and processing them for presentation in a complex with MHC class II molecules.

Activated dendritic cell: A more mature dendritic cell that expresses high levels of MHC class II, ICAM-1 and B7-2, and is capable of stimulating the proliferation of naive allogeneic T cells in a mixed leukocyte reaction (MLR).

As noted above, the present invention provides immortalized dendritic cells. The dendritic cells of the present invention are not fully differentiated, but may be stimulated to become activated dendritic cells.

Cells that can be continuously cultured and do not die after a limited number of cell generations are known as "immortalized." A cell that survives for only 20 to 80 population doublings is considered a finite or primary culture (Freshney, *Culture of Animal Cells*, Wiley-Liss, New York, 1994, herein incorporated by reference), and a cell that survives more than 80, preferably at least 100, cell generations is considered an immortalized cell. Immortalization of cells can occur spontaneously or be chemically or virally induced.

Immortalization may be associated with transformation, implying increased tumorigenicity and significant changes in phenotype, but cells may be immortalized without being tumorigenic. The altered ability to be continuously cultured may be due to, for example, a deletion or mutation in one or more of the genes whose products play a role in cell senescence, or overexpression or mutation of one or more oncogenes that override the action of the senescence genes. Expression of genes that result in positive signals for cell proliferation include SV40 large T antigen (Linder et al., *Exp. Cell Res.* 191:1–7, 1990), polyoma large T antigen (Ogris et al., *Oncogene* 8:1277–1283, 1993), adenovirus E1A (Braithwaite et al., *J. Virol.* 45:192–199, 1983), myc oncogene (Khoobyarian et al., *Virus Res.* 30:113–128, 1993), and the E7 gene of papilloma virus Type 16 (McDougall, *Curr. Top. Microbiol. Immunol.* 186:101–119, 1994).

One group of senescence genes is the tumor or growth suppressor genes. These genes are negative regulators of cell proliferation. Inactivation of growth suppressor genes is generally associated with transformation of cells and often results in tumor formation in vivo. Included in this senescence gene group are p53, RB, NF1, p16 and DCC genes (Marshall, *Cell* 64:313–326, 1991).

Animals that are "growth suppressor gene deficient" include those animals that are homozygous for a mutation in a growth suppressor gene, resulting in lack of expression of a functional growth suppressor gene product. Such mutations may arise spontaneously or be introduced. Growth suppressor gene deficient animals, such as mice and other species, may be produced, for example, by a process called homologous recombination, in which a mutated DNA sequence seeks its complement on a chromosome and then recombines to replace a portion of the native allele (Baribault et al., *Mol. Biol. Med.* 6:481–492, 1989 and Bernstein et al., *Mol. Biol. Med.* 6:523–530, 1989).

Briefly, a DNA sequence encoding a growth suppressor gene is modified to prevent expression of a functional gene product. For example, internal stop codons, deletions, frameshifts or some other modification that would terminate translation can be introduced into the DNA sequence of the growth suppressor gene along with a selectable marker. The modified sequence is transfected into embryonic stem cells, and transfected clones identified by selective pressure are screened to identify those cells that have incorporated the modified gene by homologous recombination. The cells containing the modified DNA sequence are implanted into blastocytes, which are subsequently injected into the uteri of pseudopregnant female mice, and the resulting chimeric animals are subjected to a series of back crosses to identify animals that are homozygous for the modified gene (Robertson, *Biol. of Reproduc.* 44:238–245, 1991). In the alternative, growth suppressor gene deficient animals can be obtained commercially, for example, from DNX (Princeton, N.J.), GenPharm International (Mountain View, Calif.) and The Jackson Laboratory (Bar Harbor, Me.). When an animal contains a growth suppressor gene deficiency that prevents the expression of a growth suppressor gene product, it is referred to as a "knockout" animal.

Growth suppressor genes include RB (Horowitz et al., *Proc. Natl. Acad. Sci. USA* 87:2775–2779, 1990 and Hansen et al., *Trends Genet.* 4:125–128 1988), NF1 (Cawthon et al., *Cell* 62:193–201, 1990), p16 (Marx, *Science* 264:1846, 1994) and p53 genes (Nigro et al., *Nature* 342:705–708, 1989). Other growth suppressor genes may, however, be altered to produce animals with growth suppressor gene mutations (Hiti, *Molec. Cell. Biol.* 9:4722–4730, 1989; Gallie, *J. Cell. Biochem.* 32:215–222, 1986; Alt et al., *Cold Spr. Harb. Symp. Quant. Biol.* 51:931–942, 1986; Malcolm, *Molec. Med.* 1:79–84 1984; all herein incorporated by reference). A particularly preferred growth suppressor gene is p53. The Physiological role for p53 appears to be in regulation of the cell cycle. While the precise function of the p53 protein has not been elucidated, it is thought to interact with the large T antigen and possibly be a transactivator of transcription (Donehower et al., *Nature* 356:215–221, 1992). Mutations in p53 have been correlated with increased tumorigenicity, and particularly with lung carcinomas, osteosarcomas and lymphoid tumors (Lavigueur et al., *Mol. Cell. Biol.* 9:3982–3991, 1989).

The cells of the present invention were isolated utilizing methods where a tissue was excised from a growth suppressor gene deficient animal and placed in a culture medium. Tissue is a composite of heterogeneous cell populations. Examples of tissues include bone marrow, thymus, lymph nodes, tonsils, spleen, heart, liver, skin, lung and gut. Tissues usually consist of a mixture of tissue-specific cell types, as well as non-tissue specific cells, such as fibroblasts. The preferred tissue for isolation of dendritic cells is bone marrow.

Component cells are usually isolated from tissue samples by plating cells at a density sufficiently low that colonies grow from a single cell. When necessary, the tissue is disrupted according to conventional enzymatic or mechanical methods to separate component cells. Cell populations originated from a single cell are referred to as clonal colonies or clonal cell populations.

Methods of isolating cells from tissue are known in the art. See, for example, *Methods In Molecular Biol.: Animal Cell Culture*, 5, Pollard et al. eds., Humana Press, New Jersey, 1990, which is incorporated herein by reference. For example, in addition to dendritic cells and their precursors, hematopoietic cells, such as osteoclasts, monocytes, macrophages, lymphoid cells and their precursors, may be isolated from bone marrow (for a review, see, for example, Dexter et al., in *Long-Term Bone Marrow Culture*:57–96, Alan R. Liss, 1984). Bone marrow is extracted from a sacrificed animal by dissecting out the femur, removing soft tissue from the bone and cutting off the epiphyses (cortical ends). The bone marrow is removed with a needle and syringe or flushed out with an isotonic solution. The marrow cells are plated at a low density into petri dishes and allowed to attach to the surface of the dish. Bone marrow contains several different cell types of the myeloid lineage. Therefore, dendritic cells may be identified morphologically. In one or more phases of their development, immature dendritic cells are loosely adherent to plastic, flattening out with a stellate shape. Cells have a single, rounded nucleus and lack the large granular organelles apparent in macrophages. Frequently, projections are observed protruding from both the adherent and nonadherent cells. Higher magnification reveals a "veiled" morphology.

The selection of culture medium to isolate cells of the present invention or maintain these cells or their progeny is a matter of routine experimental design and within the ordinary skill in the art. At a minimum, culture media contain a carbon source, a nitrogen source, essential amino acids, vitamins and minerals. Media may also contain such components as growth factors or serum, as required. A preferred growth medium for the dendritic cells of the present invention contains α-MEM (JRH, Lenexa, Kans.), a modified MEM (Eagle, *Science* 130:432, 1959) without ribonucleosides or deoxyribonucleosides, but containing 5–15% fetal calf serum, L-glutamine, sodium pyruvate, and granulocyte-macrophage colony stimulating factor (GM-CSF). GM-CSF should be added in concentrations of about 1–2000 U/ml, with a preferred range of 500–1000 U/ml. Other factors known to stimulate growth of dendritic cells may be included in the culture medium. Some factors will have different effects that are dependent upon the stage of differentiation of the cells, which can be monitored by testing for differentiation markers specific for the cell's stage in the differentiation pathway. It is preferred to have GM-CSF present in the medium throughout culturing. Other factors that may be desirable to add to the culture medium include, but are not limited to: granulocyte colony-stimulating factor (G-CSF; preferably at about 25–300 U/ml), monocyte-macrophage colony-stimulating factor (M-CSF; preferably at about 100–1000 U/ml), IL-1α preferably at about 1–100 LAF units/ml), IL-1β (preferably at about 1–100 LAF units/ml), IL-3 (preferably at about 25–500 U/ml), IL-6 (preferably at about 10–100 ng/ml), stem cell factor (SCF; preferably at about 10–100 ng/ml) and thrombopoietin (TPO; preferably at about 1000–10,000 U/ml). When activated dendritic cells are cultured, the medium will preferably include TNF-α (5–500 U/ml, with a preferred range of about 50 U/ml), IL-4 (0.1–10 ng/ml, preferably 10 ng/ml) and interferon-γ (25–500 U/ml, with a preferred range of about 100 U/ml).

The cell line of the present invention, through the course of continuous culturing, allows for growth and expression of immature dendritic cell functions, possibly through the expression of autocrine stimulatory factors, eliminating the need for addition of some or all exogenous growth factors to the growth medium. Because autocrine stimulatory factors are present in the medium conditioned by the cells of the present invention, this medium may be used to stimulate the growth of other dendritic cells.

Additional methods for selective growth of specific cell types include varying the substrate for cell attachment, or selective cell detachment after exposure to EDTA, trypsin or collagenase (Polinger, *Exp. Cell Res.* 63:78–82, 1970; Owens et al., *J. Natl. Canc. Inst.*, 53:261–269, 1974; Milo et al., *In Vitro* 16:20–30, 1980; Lasfargues, "Human Mammary Tumors", in Kruse et al. (eds.), *Tissue Culture Methods and Applications*, Academic Press, New York, 1973; Paul, *Cell and Tissue Culture*, Churchill Livingston, Edinburgh, 1975).

Dendritic cells have activities that are specifically associated with the maturity of the cell, i.e., its differentiated state. To identify a cell's maturity, a population of established cells is assayed and analyzed for a set of differentiation markers that are characteristic of the cell's stage in the differentiation pathway. Preferably, this is done by isolating at least a portion of the cells and subjecting this subpopulation to such analysis.

A set of differentiation markers is defined as one or more phenotypic properties that can be identified, and that are specific to a particular cell type and stage of maturity. Differentiation markers are transiently exhibited at various stages of the cell's progression toward terminal differentiation. Pluripotent stem cells that can regenerate without commitment to a specific cell lineage express a set of differentiation markers that are diminished when commitment to a particular cell lineage is made. Precursor cells express a set of differentiation markers that may or may not continue to be expressed as the cells progress down the cell lineage pathway toward maturation. Differentiation markers that are expressed exclusively by mature cells usually represent functional properties, such as cell products, enzymes to produce cell products and receptors. It is possible that with exposure to the appropriate factors, the cell line of the present invention can differentiate and mature into other cells of the monocytic cell lineage. Differentiation markers used for identifying dendritic cells include: Mac-1, F4/80, Fcγ RII/III receptor (FcR), MHC class I, MHC class II, B7-1, B7-2, ICAM-1, CD44, N418, and NLDC-145.

In immature dendritic cells, F4/80 (Lee et al., *J. Exp. Med.* 161:475, 1985) and FcR (Unkeless, *J. Exp. Med.* 150:580, 1979) are detectable, but at levels lower than those seen in a phenotypically macrophage cell using monoclonal antibodies that bind F4/80 (Caltag, San Fransisco, Calif.) and 2.4G2 for FcR binding (PharMingen, San Diego, Calif.); MHC class I is detectable using the monoclonal antibody EH144.3 (Geier et al., *J. Immunol.* 137:1239, 1986); MHC class II is detectable only at low levels using the monoclonal antibody AF6-120.1 (PharMingen); B7-1 and B7-2 are detectable at low levels (Nabavi et al., *Nature* 360:266, 1992 and Hathcock et al., *Science* 262:905, 1993, respectively) using monoclonal antibodies IG10 (PharMingen) and GL1 (PharMingen); ICAM-1 (Rothlein et al., *J. Immunol.* 137:1270, 1986), using monoclonal antibody 3E2 (PharMingen), and CD44 (Lesley et al., *Immunogenetics* 15:313, 1982), using monoclonal antibody IM7 (PharMingen), are detectable at high levels; and at least one of the dendritic cell markers CD11c (Metaly et al., *J. Exp. Med.* 171:1753, 1990), using the monoclonal antibody N418, or DC-205 (Kraal et al., *J. Exp. Med.* 163:981, 1986), using the monoclonal antibodies NLDC-145 (Accurate Chem. and Scientific, Westbury, N.Y.) and 33D1 (Nussenzweig et al., *Proc. Natl. Acad. Sci. USA.* 79:161, 1982), should be detectable. The skilled practioner would recognize that not all of these differentiation markers may be present and that expression levels may vary.

In activated dendritic cells, high levels of MHC class II are detectable; B7-2 and ICAM-1 are expressed at higher levels, and F4/80 is expressed at lower levels than seen in immature dendritic cells.

Analyses of the cell surface using monoclonal antibodies are made using a flow cytometer, see, for example, Fink et al., *J. Exp. Med.* 176:1733, 1992 and Crowley et al., *Cellular Immunol.* 118:108–125, 1989. Briefly, the cells are either combined with monoclonal antibodies directly conjugated to fluorochromes, or with unconjugated primary antibody and subsequently with commercially available secondary antibodies conjugated to fluorochromes. The stained cells are analyzed using a FACScan (Becton Dickinson, Mountain View, Calif.) using LYSYS II or Cell Quest software (Becton Dickinson).

Identification of activated dendritic cells is confirmed by the cells' ability to stimulate the proliferation of allogeneic T cells in a MLR. Briefly, activated dendritic cells are incubated with allogeneic T cells in a 96-well microtiter dish (American Scientific Products, Chicago, Ill.). Stimulation of the T cells to proliferate is measured by incorporation of $^3$H-thymidine. It is preferred to expose the dendritic cells of the present invention to irradiation to slow the proliferation of the dendritic cells and reduce background in the assay caused by incorporation of $^3$H-thymidine by the dendritic cells.

In addition, Mac-1 is a marker of differentiation for monocytic lineage cells that include dendritic cells, macrophage and osteoclast precursor cells (MacCormack et al., *J. Immunol.* 151:6389–6398, 1993, and Gordon et al., *Current Opin. in Immunol.* 4(25):25–32, 1992). Thus, the Mac-1 marker may be indicative of a dendritic cell precursor. The cell line of the present invention expresses Mac-1, but at levels lower than expected for a typical macrophage cell.

After a subset of cells expressing a set of differentiation markers of interest is identified, a portion of the subset is passaged for at least 80 cell generations, preferably 100 cell generations, to establish that the cells are immortalized. Cells not used to establish that the cell line is immortal can be passaged for an appropriate number of cell generations then be stored using conventional methods well known to those ordinarily skilled in the art. For example, cells may be frozen in growth medium or in serum with 15% dimethylsulfoxide (DMSO) added at a temperature of −80° C. or lower.

Immortalized precursor and immature dendritic cells can be stimulated to differentiate and to provide activated dendritic cells. Differentiation is induced by exposing the undifferentiated stem cells, precursor cells or immature dendritic cells to factors that are specific to a cell's stage in the differentiation pathway. For example, dendritic cells can be exposed to GM-CSF, TNF-α, IL-4 and/or interferon-γ (Scheicher et al., *J. Immunol. Meth.* 154:253, 1992; Caux et al., *Nature* 360:258–261, 1992; Reid et al., *J. Immunol.* 149:2681–2688, 1992; Lutz et al., *J. Immunol. Meth.* 174:269–279, 1994; Knight et al., *J. Invest. Dermatol.* 99:33S–38S, 1992; and Aiello et al., *J. Immunol.* 144:2572–2581, 1990) to induce differentiation in dendritic cells from immature cells to activated dendritic cells.

Once an immortalized cell line has been established, genetic material from the cells may be used to construct cDNA libraries. Methods for preparing cDNA libraries are well known in the art. See, for example, Sambrook et al., *Molecular Cloning: A Laboratory Manual*, 2nd ed., Cold Spring Harbor Laboratory Press, Cold Spring Harbor, N.Y., 1989 and Ausabel et al., eds., *Current Protocols in Molecular Biology*, John Wiley and Sons, Inc. New York, 1987. By selecting cells at various stages of differentiation, the biological functions that are associated with a specific stage in the differentiation pathway may be identified once a cDNA library is prepared from that cell's mRNA. The libraries may be used to clone novel factors produced by specific cell types, such as differentiation factors, growth hormones, and other cytokines and growth factors.

Cell lines prepared by the methods of the present invention may also be used to prepare a protein library. A protein library is complementary to the cDNA library. Amino acid sequence information obtained from the protein library enables rapid isolation of cDNAs encoding proteins of interest. The use of protein sequence data to design primers for DNA isolation eliminates problems arising in conventional library preparation methods due to relative mRNA abundance. Coupling of protein and cDNA libraries also facilitates the targeted cloning of sequences of particular interest. A protein library is prepared by extracting protein (total proteins or fractions of interest) from cells according to known methods, then separating the proteins by two-dimensional gel electrophoresis. Isolated proteins are then subjected to in situ tryptic digestion followed by separation by micro-bore HPLC. The separated fragments are then analyzed by mass spectrometry. The resulting mass profile is searched against a protein sequence data base to infer protein identity. Unidentified peptides can be sequenced by Edman degradation. The resulting cDNA and protein libraries are valuable sources of new proteins and the sequences encoding them.

The cells of the present invention may also be used for screening agonists and antagonists of compounds and factors that affect the various metabolic pathways of a specific cell. For example, cells of the dendritic lineage may be used to screen for molecules that enhance or inhibit dendritic growth or differentiation or antigen presentation itself. In addition, the cells of the present invention may be used to generate antibodies for cell-specific proteins, elucidate the interactions between cell types and cell matrix components, and may be used for expressing foreign genes. For example, antibodies to cell-surface markers may be generated and used to purify a subpopulation from a heterogenous population of cells using a cell sorting system. Using membrane fragments from cells of the present invention, monoclonal antibodies are produced according to methods known in the art (Kohler et al., *Nature* 256: 495, 1975; Kohler et al., *Eur. J. Immunol.* 6: 511–519, 1976; and Hurrell, ed., *Monoclonal Hybridoma Antibodies: Techniques and Applications*, CRC Press Inc., Boca Raton, Fla., 1982) and screened using a variety of cell lines to identify antibodies that display cell specificity. In addition, cell specific monoclonal antibodies can be used to purify cell-surface markers and identify their function. Stem cells and precursor cells can be marked, for example, using β-galactosidase, and their ontogeny followed in heterogenous cell and nutrient environments.

Because dendritic cells can take up, process and present exogenous antigen (including proteins, glycoproteins and peptides), these cells are valuable tools that can be used to identify dominant epitopes of a particular antigen. Such epitope mapping can be attempted by repeated testing with large numbers of defined synthetic peptides, but this process is inefficient, tedious, and not necessarily a mimic of natural antigen processing by antigen presenting cells. The dendritic cells described and claimed herein will naturally process and present exogenous protein, permitting epitope mapping studies that better mimic the in vivo, natural process. At present, the only means available for epitope mapping of naturally processed antigen are EBV-transformed B cells (which are inefficient at taking up (i.e., endocytosing) and processing proteins, and are limited to peptide processing and presentation) and peripheral blood mononuclear cells (PBMNs; a heterogeneous population including B and T lymphocytes, monocytes and dendritic cells).

Moreover, the dendritic cells herein can be used to stimulate naive T cells, as well as primed T cells. This characteristic is unique to dendritic cells, and thus is not available through use of EBV-transformed B cells, for instance.

The dendritic cells of the present invention can be advantageously used in antigen-specific lymphocyte activation assays. To generate activated dendritic cells, it is preferred that activators be incubated with immature dendritic cells for about 1 to 48 hours, most preferably 3 hours.

The dendritic cells are activated to induce expression of MHC class II molecules on the cell surface, making these mature dendritic cells competent for antigen processing and presentation. These activated cells (i.e., stimulators) are then exposed to antigen for a time sufficient for antigen presentation. One skilled in the art would recognize that the time required for endocytosis, processing and presentation of antigen is dependent upon the proteinaceous antigen being used for this purpose. Methods for measuring antigen uptake and presentation are known in the art. For example, dendritic cells can be incubated with a soluble protein antigen (e.g., ovalbumin or conalbumin) for 3–24 hours then washed to remove exogenous antigen.

These antigen-presenting stimulator cells are then mixed with responder cells, preferably naive or primed T lymphocytes. After an approximately 72 hour incubation (for primed T lymphocytes) or approximately 4–7 d period (for naive T lymphocytes), the activation of T cells in response to the processed and presented antigen is measured. In a preferred embodiment, T cell activation is determined by measuring T cell proliferation using $^3$H-thymidine uptake (Crowley et al., *J. Immunol. Meth.* 133:55–66, 1990). The responder cells in this regard can be PBMN cells, cultured T cells, established T cell lines or hybridomas. Responder cell activation can be measured by the production of cytokines, such as IL-2, or by determining T cell-specific activation markers. Cytokine production can be assayed by the testing the ability of the stimulator+responder cell culture supernatant to stimulate growth of cytokine-dependent cells. T cell-specific activation markers may be detected using antibodies specific for such markers.

For T cell proliferation assays, it is preferred to inhibit the proliferation of dendritic cells prior to mixing with T responder cells. This inhibition may be achieved by exposure to gamma irradiation or to an anti-mitotic agent, such as mitomycin C.

Alternatively, activated dendritic cells can be used to induce non-responsiveness in T lymphocytes. In addition to MHC class II recognition, T cell activation requires co-receptors on the antigen-presenting cell (APC; e.g., dendritic cell) that have been stimulated with co-stimulatory molecules. By blocking or eliminating stimulation of such co-receptors (for instance, by blocking with anti-receptor or anti-ligand antibodies, or by "knocking out" the gene(s) encoding such receptors), presentation of antigen by co-receptor-deficient dendritic cells can be used to render T lymphocytes non-responsive to antigen.

For some applications, it is preferable to genetically manipulate the dendritic cells so that they overexpress MHC class II molecules at their surface.

In yet another embodiment, the dendritic cells of the present invention can be transfected with a polynucleotide encoding a heterologous protein involved in antigen presentation to responder cells. In a preferred embodiment, the dendritic cells are transfected with a polynucleotide encoding a selected MHC class II molecule of interest. Any MHC class II molecule of mammalian origin may be used in this regard, with MHC class II molecules associated with a particular disease preferred. Human MHC class II molecules associated with autoimmune diseases, and especially those associated with diabetes (e.g., DR4, DR3, DQ2 and DQ8), are particularly preferred. It is also preferred that endogenous MHC class II molecules are blocked or eliminated, thereby providing an APC cell that expresses or overexpresses only one type of MHC class II on its surface. Blocking may be achieved using antibodies directed against endogenous MHC class II; however, heterodimers of endogenous and heterologous MHC class II chains may not be blocked and may provide anomalous results. More preferably, the coding region for endogenous MHC class II is eliminated, such as by gene disruption by means of homologous recombination.

For instance, dendritic cells of the present invention can be transfected with a polynucleotide encoding human DR4. The genes encoding endogenous MHC class II molecules (i.e., I-A and I-E) are eliminated by homologous recombination, so that only human DR4 can be expressed by the transfected cells. These DR4-expressing dendritic cells are activated to induce cell surface expression of DR4, and exposed to exogenous glutamic acid decarboxylase (GAD) antigen. After a time sufficient for natural antigen endocytosis, processing and presentation, the antigen-presenting, transfected cells are combined with responder cells. In a preferred embodiment, these responder cells are PBMN cells obtained from patients with diabetes.

At this point, the responder T cells can be selectively amplified and/or stimulated, thereby producing a subset of T cells that are specific for GAD and restricted by the DR4 allele. For instance, DR4-expressing T cells may be selected by flow cytometry, and particularly by fluorescence activated cell sorting. This subset of DR4-restricted T cells can be maintained by repetitive stimulation with DR4-expressing dendritic cells presenting GAD antigen. Alternatively, T cell clones can be established from this T cell subset. Further, this subset of T cells can be used to map GAD epitopes, and to define relevant GAD peptides that are presented by DR4 on the APC.

Alternatively, MHC class II molecules identified in model systems of autoimmune disease may be further studied by transfecting a polypeptide encoding the disease-associated MHC class II molecules into the dendritic cells. For instance, a polynucleotide encoding I-A$^{g7}$ MHC class II molecules of NOD mice, a model system for insulin-dependent diabetes mellitus (IDDM), can be transfected into the dendritic cells. Such I-A$^{g7}$ expressing dendritic cell may be a useful research reagent, particularly because this APC is homogeneous and provides "off the shelf" availability. Further, an I-A$^{g7}$ expressing dendritic cell can be used in conjunction with dendritic cells transfected with human diabetes-related MHC class II molecules, to better identify the strengths and limitations of the model system.

The dendritic cells of the present invention also provide a stable, reproducible, homogeneous population of cells that can be cultured and obtained in significant numbers. The low frequency of dendritic cells in mononuclear cell preparations has prevented extensive molecular, biochemical and physiological study of this unique type of APC. The claimed cell line permits, for the first time, an examination of molecules, including polynucleotides and proteins, that may be uniquely expressed in dendritic cells. More particularly, these dendritic cells will permit identification and analyses of genes, proteins, metabolic and proteolytic processes, as well as other molecules and processes, that enable dendritic cells to be such potent APCs. The molecules and processes involved in endocytosis are of interest, since dendritic cells are particularly effective at taking up exogenous antigen. The molecules and processes involved in antigen processing are also of interest, since dendritic cells are uniquely able to process exogenous antigen for presentation. Related cell components and their interaction with molecules and processes involved in antigen uptake, processing and presentation can also be dissected. For instance, these dendritic cells can be used to examine one or a set of co-stimulatory molecules, and to determine whether unique properties or interactions of these co-stimulatory molecules contribute to the superior antigen processing and presenting characteristics of dendritic cells. Likewise, other components that play a role in cellular immunology (for instance, DM genes and invariant chain) may be analyzed in this setting. Furthermore, this homogeneous dendritic cell line can be used as an immunogen to identify lineage-specific markers for dendritic cells.

The invention is illustrated by the following non-limiting examples.

EXAMPLES

The isolated cell line designated JAWS II, and deposited on May 31, 1995 as CRL-11904 at the American Type Culture Collection (12301 Parklawn Drive, Rockville, Md.), was identified as a monocytic lineage cell expressing dendritic cell phenotype according to the following methods:

Example I

MAC-1 Antigen

Mac-1 is a cell surface antigen expressed by monocytes, granulocytes and macrophages, but not by mature osteoclasts. Mac-1 positive cells were identified using a rat monoclonal antibody to Mac-1 (Boehringer Mannheim, Indianapolis, Ind.).

Cells were plated at a density of $5 \times 10^4$ cells/well on an 8-chamber slide (Nunc, Naperville, Ill.) and allowed to grow for 1 week to 10 days at 37° C. and 5% $CO_2$ in 500 µl of growth medium with $10^{-8}$M $1\alpha,25$-dihydroxycholecalciferol and $10^{-7}$M dexamethasone added to promote differentiation. The medium was removed, and the cells were washed in PBS. The wells were rinsed in phosphate buffered solution (PBS) with 1 mg/ml bovine serum albumin (BSA) added, and fixed in Z FIX (Anatech Ltd., Battle Creek, Mich.) for 10 minutes. After fixing, the wells were rinsed in PBS/BSA solution. The chambers were removed, retaining the gaskets on the slides. The anti-Mac-1 antibody was diluted 1:20 in the PBS/BSA solution, and 25 µl/well of the antibody solution was added to each well and incubated for 45 minutes at room temperature. After incubation, the wells were rinsed three times in the PBS/BSA solution. Twenty-five microliters of goat FITC-anti-rat IgG (Boehringer Mannheim) diluted 1:50 in PBS/BSA solution was added to each well and incubated for 45 minutes at room temperature in the dark. The wells were rinsed three times in PBS/BSA solution and a final rinse in water was done. The gaskets were removed and a coverslip was mounted on the slide using mounting solution prepared using 9 parts of 2% 1,4 diazobicyclo(2,2,2)-octane in glycerol (Sigma, St. Louis, Mo.) that was dissolved at 70° C. and 1 part 0.2M Tris-HCl and 0.02% $NaN_3$ (pH 7.5) to prevent fading. Cultures of JAWS II expressed Mac-1 on their cell surface.

Example II

Calcitonin binding assay

The JAWS II cell line was assayed for the presence of the calcitonin receptor by binding of calcitonin. The subcloned cells were plated at a density of $5 \times 10^4$ cells/well on an 8-chamber slide (Nunc, Naperville, Ill.) and allowed to grow for 1 week to 10 days at 37° C. and 5% $CO_2$ in 500 µl of growth medium with $10^{-8}$M $1\alpha,25$-dihydroxycholecalciferol and $10^{-7}$M dexamethasone added to promote differentiation. The medium was removed, and the cells were washed in PBS. Three hundred microliters of binding medium (RPMI (Fred Hutchinson Cancer Research Center, Seattle, Wash.) and 0.1% BSA) was added to each well. Three hundred microliters of binding medium containing 0.2 nM $^{125}$I radiolabeled salmon calcitonin with a specific activity of approximately 1000 Ci/mmole (Peninsula, Belmont, Calif.) were added to half the wells, and 300 µl of binding medium containing 0.2 nM $^{125}$I salmon calcitonin and 1 µM unlabeled salmon calcitonin were added to the remaining wells. The slides were incubated for 1.5 hours at room temperature, then rinsed 3 times with PBS to remove unincorporated radioactivity. The slides were immediately prepared for TRAP staining.

Example III

TRAP staining

Osteoclasts express a tartrate resistant form of acid phosphatase (TRAP). TRAP staining detects cells that are tartrate resistant by formation of an insoluble red stain. Slides that had been treated for calcitonin receptor analysis (Example II) were fixed by adding 100 µl of a solution containing 2.5% glutaraldehyde and 3.5% formaldehyde in PBS for 10 minutes. After the glutaraldehyde/formaldehyde solution was removed, 100 µl of a 1:1 acetone/ethanol solution was added for 1 minute. An Acid Phosphatase, Leukocyte Kit (Sigma, St. Louis, Mo.) was used to prepare a substrate solution containing 45 ml of deionized water at 37° C., 1.0 ml of Diazotized Fast Garnet GBC solution (0.5 ml Fast Garnet GBC Base solution and 0.5 ml sodium nitrite solution), 0.5 ml Naphthol AS-BI Phosphate solution, 2.0 ml Acetate solution and 1.0 ml tartrate solution according to the manufacturer's specifications. Approximately 100 µl of the substrate solution was added to each well. The plates were incubated at 37° C. for 30–60 minutes. The stain was removed and the plates were washed gently with tap water. The slides were examined microscopically for TRAP positive cells. After examination, the slides were dipped in Kodak NTB3 emulsion (Kodak, Rochester, N.Y.) and allowed to air dry. The slides were placed at 4° C. for 12 days in the dark and developed in Kodak D19 developer (Kodak). After being developed, the slides were fixed in RAPID FIX (Kodak) for 5 minutes. An analyzed subpopulation of the JAWS II cell line did not express the calcitonin receptor, and was positive for expression of tartrate-resistant acid phosphatase.

Example IV

NSE Staining for Identification of Monocyte/Macrophage Lineage

The Nonspecific Esterase (NSE) assay uses specific esterase substrates in defined reaction conditions to distinguish granulocytes from monocytes. Cells of the monocyte lineage include dendritic cells, macrophages and osteoclasts. Bone marrow cultures are incubated with alpha-naphthyl acetate in the presence of a stable diazonium salt. Enzymatic hydrolysis of ester linkages liberates free naphthol compounds. The naphthol compounds couple with the diazonium salt, forming highly colored deposits at the sites of enzyme activity.

Cells were plated at $5 \times 10^4$ cells/well on an 8-chamber slide (Nunc). The cells were affixed to the slides in Citrate-Acetone-Methanol Fixative for 1 minute at room temperature. The fixative was prepared using 18 ml of citrate dilute solution (0.383M citrate buffer pH 5.4, diluted at 1 part citrate buffer to 9 parts deionized water, pH 5.4), 27 ml ACS grand acetone and 5 ml methanol. After fixation, the slides were washed thoroughly in deionized water and air dried for at least 20 minutes. A capsule of FAST BLUE RR SALT (Sigma, St. Louis, Mo.) was added to 50 ml of TRIZMAL 7.6 Dilute Buffer Solution (Sigma) in a Coplin jar. One part TRIZMAL 7.6 Buffer concentrate is diluted with 9 parts deionized water to make the dilute solution. When the salt was dissolved, 2 ml of alpha-naphthyl acetate solution (Sigma) was added and stirred for 15–20 seconds. Specimen slides were added to the jar and incubated for 30 minutes at 37° C. The slides were removed from the stain and washed for 3 minutes in deionized water, air dried and examined microscopically. NSE positive cells were seen in JAWS II cultures, with and without the addition of 1α,25-dihydroxycholecalciferol, indicating the presence of cells of the monocytic lineage.

Example V

Characterization of Bone Resorptive Activity

Bovine cortical bone wafers were cut on a Buehler 11-1180 isomet low speed saw (Buehler, Lake Bluff, Ill.). The slices were measured and sterilized using ethanol and ultraviolet light exposure overnight. The wafer sizes varied between 0.1–0.19 mm. The wafers were rinsed in PBS and stored hydrated in growth medium at 37° C. in 5% $CO_2$. The wafers were placed in 8-chamber slides (Nunc), and cells were plated on the wafers at a density of $5 \times 10^4$ cells/well. The medium was changed every four days. On day 10, the medium was changed to low pH α-MEM with 0.7 g/L $NaHCO_3$, $10^{-8}$M 1α,25-dihydroxycholecalciferol and $10^{-7}$M dexamethasone added. On day 12 the medium was removed, trypsin/EDTA solution was added overnight, and the wafers were sonicated to remove the cells from the wafers. The wafers were rinsed in PBS and stained with 1% Toluidine Blue and 1% sodium borate for 1 minute. The excess stain was removed by washing with PBS followed by water. The wafers were viewed under an inverted scope at 10× magnification for quantitation of resorption pits using the Optimas Image Analysis program (Bioscan, Edmonds, Wash.). Results of the microscopy demonstrate that JAWS II cultures did not resorb bone.

Example VI

FACScan Analysis of the Cell Surface

Analyses of the cell surface proteins of JAWS II was made using FACScan (Becton Dickinson) using LYSYS II or Cell Quest software (Becton Dickinson) according the manufacturer's specifications.

Approximately $10^6$ cells were incubated at 4° C. for 15–20 minutes in BSS-BSA (Hank's buffered salts solution which contains 0.0345% sodium bicarbonate, 5 mM HEPES, 1% bovine serum albumin) containing primary antibody. The primary antibody solution was removed, and the cells were washed with BSS-BSA and resuspended in phosphate-buffered saline (PBS). If the primary antibody was not conjugated with a fluorochrome, then the washed cells were similarly incubated at 4° C. with a fluorochrome-conjugated secondary antibody before washing and resuspension in PBS.

The results, shown in Table 1, demonstrate that JAWS II has cell-surface markers associated with the phenotype of an immature dendritic cell, and when induced (as described in Example VIII) with combinations IFN-γ, TNF-α and IL-4, the cells exhibit markers associated with activated dendritic cells. The splenic dendritic cells are from C57Bl/6 mice (Jackson Labs) and were isolated (as activated dendritic cells) using preferential adherence and detachment to plastic, as described by Swiggard et al. (*Curr. Protocols Immunol.* 3.7.1–3.7.11, 1992).

TABLE 1

| Surface proteins/antigens | (mAb) | JAWS II | Splenic DC (B6 mice) |
|---|---|---|---|
| 1 MHC class I | EH144.13 | High | High |
| 2 MHC class II | AF6-120.1 | negative/low | High |
| 3 MHC Class II + IFN gamma | | High | NT |
| 4 B7-1/BB1 (CD80) | 1G10 | negative/low/ | negative/low/ |

TABLE 1-continued

| Surface proteins/antigens | (mAb) | JAWS II | Splenic DC (B6 mice) |
|---|---|---|---|
| 5 B7-1/BB1 + IFN-gamma |  | intermed Decreased | intermed. NT |
| 6 B7-2 (CD86) | GL1 | negative/flow/ intermed. | low/intermed. |
| 7 B7-2 + IFN-gamma/TNF-alpha/IL-4 |  | Increased (low/intermed.) | NT |
| 8 ICAM-1(CD54) | 3E2 | Intermed | High |
| 9 ICAM-1 + IFN-gamma/TNF-alpha/IL-4 |  | High | NT |
| 10 DC-205 | NLDC-145 | Intermed. | negative/low/ Intermed. |
| 11 |  |  | (intermed./ high in BALB/c DC) |
| 12 Mac-1 (CD11b) | M1/70- | High | negative/low |
| 13 Fc-gamma-RII/III receptor | 2.4G2 | High | negative/low |
| 14 F4/80 | F4/80 | High | Low |
| 15 F4/80 + IL-4 |  | Decreased somewhat | NT |
| 16 Pgp-1 (CD44) | IM7 | High | High |
| 17 HSA (Heat Stable Antigen; CD24) | M1/69 | High | High |
| 18 B220 (B cell antigen) | RA3-6B2 | negative | negative |
| 19 Thy1 (T cell antigen) | TS | negative | negative |
| 20 CD4 (T cell antigen) | RM4-5 | negative | negative |
| 21 CD8 (T cell antigen) | 53-6.7 | negative | negative |
| 22 Plastic adherence |  | Low | Low |
| 23 Stimulation of allo-MLR |  | Low | Very High |
| 24 allo-MLR + IFN-gamma/TNF-alpha/IL-4 |  | High | NT |

Example VII
Mixed Lymphocyte Reaction (MLR)
A. Preparation of stimulator cells (dendritic cells)

JAWS II cells were grown to high density (1–2×10$^6$ cells/ml) in α-MEM (Minimal Essential Medium, alpha-modification, containing 10% fetal bovine serum (FBS), 1 mM sodium pyruvate, 4 mM glutamine)+5 ng/ml murine GM-CSF. Additional cytokines used to activate the cells included interferon-γ (100 U/ml), tumor necrosis factor-α (10 ng/ml), and interleukin-4 (10 ng/ml). The culture supernatant containing the nonadherent cells was pooled with adherent cells removed by washing with Versene and the cells were resuspended at 3×10$^5$ cells/ml in RPMI-1640 medium (containing 10% FBS, 10 mM HEPES, 4 mM glutamine, 5.7×10$^{-5}$M 2-mercaptoethanol, 50 µg/ml gentamycin, 100 U/ml penicillin, 100 µg/ml streptomycin).

Splenic dendritic cells were isolated by the method of Swiggard et al. (*Curr. Protocols Immunol.* 3.7.1–3.7.11, 1992) from spleens of C57Bl/6 and BALB/c mice. Briefly, single cell suspensions of spleen cells were generated by digestion with collagenase and a low density fractionation. The low density fraction was obtained by centrifugation of the cells through a low density solution (refractive index of approximately 1.364) of bovine serum albumin (BSA) in phosphate-buffered saline (PBS) onto a high density cushion (refractive index of approximately 1.385) of BSA in PBS and contained primarily dendritic cells, macrophages, and some B cells. Cells were resuspended at 37° C. in RPMI medium at 1×10$^7$ cells/ml and 4 ml of the suspension was plated per 60 mm tissue culture plate. After a 90 minute incubation at 37° C., nonadherent cells were gently removed, adherent cells were washed with RPMI, and incubated in RPMI for an additional 30–60 min. Nonadherent cells were again removed and adherent cells gently washed with RPMI and incubated in RPMI for 12–20 hours at 37° C. Splenic dendritic cells detached during the final incubation and were isolated as nonadherent cells. The nonadherent splenic dendritic cells were resuspended in RPMI at 3×10$^5$ cells/ml.

JAWS II and splenic dendritic stimulator cells were irradiated for 40 minutes in a $^{137}$Cs irradiator (GAMMACELL 40, Nordion International Inc., Kanata, Ontario, Canada) at 550 rads/min before use in the MLR.

B. Preparation of responder cells (T cells)

Spleens and lymph nodes were removed from C57Bl/6 or BALB/c mice (Jackson Labs, Bar Harbor, Me.). Spleen cell suspensions in BSS-BSA buffer were made by mechanical disruption of the spleen between glass slides. Red blood cells were lysed by resuspending the spleen cell pellet in 0.9 ml dH$_2$O followed quickly by addition of 0.1 ml 10× HBSS. Lymph node cell suspensions in BSS were made by teasing the nodes with sterile forceps and were pooled with the autologous spleen cell suspension and filtered through nylon cloth filters to remove debris.

The single cell suspension of spleen and lymph node cells was loaded onto a nylon wool column pre-equilibrated at 37° C. with BSS+5% FBS. After incubation at 37° C. for 45 minutes, the T cells were eluted with 37° C. BSS+5% FBS (12 ml per 1.5 g nylon wool column loaded with approximately 1.5×10$^8$ total spleen+lymph node cells). The T cells (usually 80–90% pure) were resuspended in RPMI at 3×10$^6$ cells/mL.

C. Incubation conditions for MLR

3×10$^5$ responder cells per well (96-well plate) were mixed in duplicate with increasing numbers of irradiated stimulator cells (usually 3×10$^3$, 1×10$^4$, 3×10$^4$ cells) in a final volume of 200 µl. Controls included responder cells alone and stimulator cells alone. A syngeneic MLR includes responder and stimulator cells from the same mouse strain (e.g., C57Bl/6 or BALB/c), whereas an allogeneic MLR has stimulator cells incubated with responder cells from a different strain (e.g., C57Bl/6 or JAWS II stimulator cells with BALB/c responder cells). The MLR cultures were incubated at 37° C. for approximately 72–76 hours before addition of 1 µCi/well $^3$H-thymidine to assay proliferation of responder cells. Cultures were harvested 16–20 hours later with a Skatron cell harvester (Skatron, Sterling, Va.), and the incorporated $^3$H-thymidine was determined with a Wallac Betaplate liquid scintillation counter (Pharmacia).

The results, illustrated in the Figure, demonstrate that when JAWS II cells are induced with a combination of factors they will stimulate allogeneic T cells to proliferate. The degree of stimulation is dependent upon the factors used to induce activation of the cell line. The Figure shows that stimulation of allogeneic T cells is highest when JAWS II is induced with TNF-α, IFN-γ, GM-CSF and IL-4. In addition, the JAWS II cell line did not stimulate proliferation in syngeneic T cells.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

We claim:

1. A dendritic cell line, wherein said cell line is deposited at the ATCC as JAWS II. (ATCC accession # CRL-11904).

2. An activated dendritic cell line, wherein the dendritic cell line of claim 1 is induced.

3. The activated dendritic cell line of claim 2, wherein the cell line is induced using a factor selected from the group consisting of:

(a) tumor necrosis factor-α (TNF-α);
   (b) interferon-γ (IFN-γ);
   (c) granulocyte macrophage colony-stimulating factor (GM-CSF);
   (d) interleukin-4 (IL-4); and
   (e) a combination of (a), (b), (c) or (d).

4. A method for in vitro assay of antigen-specific responder cell stimulation comprising:

activating JAWS II dendritic cells (ATCC # CRL-11904);
   exposing said activated JAWS II dendritic cells to an exogenous antigen, thereby producing antigen-presenting stimulator cells;
   inhibiting proliferation of said antigen-presenting stimulator cells by exposure to γ irradiation or to mitomycin C;
   combining said antigen-presenting stimulator cells with responder cells; and
   measuring activation of the responder cells.

5. The method of claim 4, wherein the responder cells are naive or primed T lymphocytes.

6. The method of claim 4, wherein the activation of the responder cells is determined by measuring responder cell proliferation.

7. A method for obtaining a dendritic cell that expresses a heterologous MHC class II protein at the cell surface comprising:

transfecting JAWS II dendritic cells (ATCC # CRL-11904) with a polynucleotide encoding a heterologous MHC class II protein; and
   selecting a subset of the dendritic cells that expresses the heterologous MHC class II protein at the cell surface, thereby forming selected MHC class II-specific dendritic cells.

8. The method of claim 7, further comprising, after the step of selecting, the step of:

eliminating from the dendritic cell genome any region that encodes endogenous MHC class II molecules.

9. The method of claim 7, further comprising, after the step of selecting, the step of:

activating the selected MHC class II-specific dendritic cells.

10. The method of claim 9 further comprising, before, during or after the step of activating, the step of:

blocking endogenous MHC class II protein expressed by the selected MHC class II-specific dendritic cells.

11. The method of claim 9 further comprising, after the step of activating, the steps of:

exposing the selected MHC class II-specific dendritic cells to an exogenous antigen, thereby producing selected MHC class II-specific antigen-presenting stimulator cells;
    combining the selected MHC class II-specific antigen-presenting stimulator cells with responder cells; and
    measuring stimulation of the responder cells.

12. The method of claim 11, wherein the responder cells are T lymphocytes.

13. The method of claim 11, wherein the exogenous antigen is a self or non-self antigen that is involved in a T lymphocyte-mediated response.

14. The method of claim 11, wherein the exogenous antigen is an autoantigen.

15. The method of claim 11, wherein the exogenous antigen is glutamic acid decarboxylase (GAD) and the heterologous MHC class II protein is an MHC molecule associated with diabetes.

* * * * *